United States Patent [19]
Luther et al.

[11] Patent Number: 4,950,252
[45] Date of Patent: Aug. 21, 1990

[54] SINGLE HAND ACTUATED LOCKING SAFETY CATHETER AND METHOD OF USE

[75] Inventors: Ronald B. Luther, Newport Beach; Pradip V. Choksi, Northridge, both of Calif.

[73] Assignee: Luther Medical Products, Inc., Tustin, Calif.

[21] Appl. No.: 191,286

[22] Filed: May 5, 1988

Related U.S. Application Data

[63] Continuation-in-part of Ser. No. 115,407, Nov. 2, 1987, Pat. No. 4,832,696, which is a continuation-in-part of Ser. No. 22,132, Mar. 5, 1987, Pat. No. 4,762,516.

[51] Int. Cl.⁵ ............................................. A61M 5/00
[52] U.S. Cl. .................................. 604/198; 604/164
[58] Field of Search ........................ 604/164–169, 604/158, 162, 263, 192, 198, 110, 51–53

[56] References Cited

U.S. PATENT DOCUMENTS

| | | | |
|---|---|---|---|
| 3,463,152 | 8/1969 | Sorenson | 128/214.4 |
| 3,536,073 | 10/1970 | Farb | 128/214.4 |
| 4,108,175 | 8/1978 | Orton | 604/900 |
| 4,160,450 | 7/1979 | Doherty | 128/214.4 |
| 4,500,312 | 2/1985 | McFarlane | 604/263 |
| 4,588,398 | 5/1986 | Daugherty et al. | 604/265 |
| 4,631,057 | 12/1986 | Mitchell | 604/198 |
| 4,664,653 | 5/1987 | Sagstetter et al. | 604/197 |
| 4,664,654 | 5/1987 | Strauss | 604/198 |
| 4,676,783 | 6/1987 | Jagger et al. | 604/171 |
| 4,702,738 | 10/1987 | Spencer | 604/198 |
| 4,747,831 | 5/1988 | Kulli | 604/198 |
| 4,762,516 | 8/1988 | Luther | 604/198 |
| 4,781,692 | 11/1988 | Jagger et al. | 604/171 |
| 4,828,549 | 5/1989 | Kualo | 604/164 |
| 4,832,696 | 5/1989 | Luther et al. | 604/164 |

FOREIGN PATENT DOCUMENTS

| | | | |
|---|---|---|---|
| 0023580 | 2/1981 | European Pat. Off. | 604/177 |
| 0139872 | 7/1984 | European Pat. Off. | |
| 0138972 | 8/1985 | European Pat. Off. | 604/168 |

OTHER PUBLICATIONS

"Introducing the ICU High Risk Needle" by ICU Medical, Inc. of 3 pages.

Primary Examiner—C. Fred Rosenbaum
Assistant Examiner—Denise W. DeFranco
Attorney, Agent, or Firm—Stetina and Brunda

[57] ABSTRACT

An assembly of a needle, catheter, and a device for selectively protecting the needle tip from inadvertent needle sticks is disclosed, characterized by use of elongate housing, having a needle extending therefrom, and a needle guard adapted for sliding movement relative the housing. The needle guard is formed to carry a catheter hub and catheter thereupon, and includes an actuation tab to enable selective sliding movement of the needle guard relative the housing and along the length of the needle. The housing is adapted to be held within one hand to permit insertion of the needle and catheter into a patient, and after insertion, the needle may be withdrawn from the patient and covered by the needle guard merely by pressing against the actuation tab with the index finger of the hand of a user, while slidably retracting the housing and needle relative the needle guard by use of the thumb and middle finger. Upon full retraction of the housing relative the needle guard, a detent mechanism formed between the housing and needle guard is engaged, to permanently lock the needle guard about the length of the needle and prevent accidental contact with the tip of the needle.

21 Claims, 2 Drawing Sheets

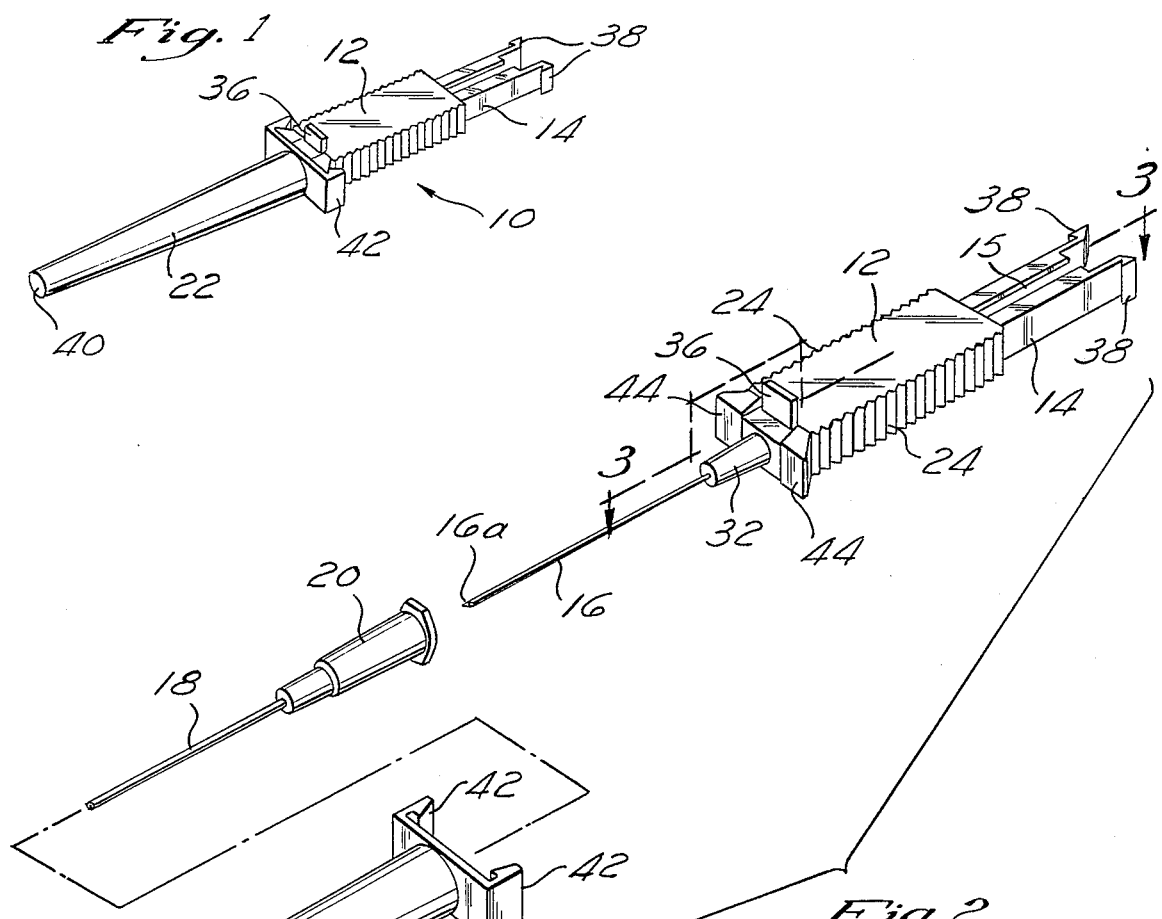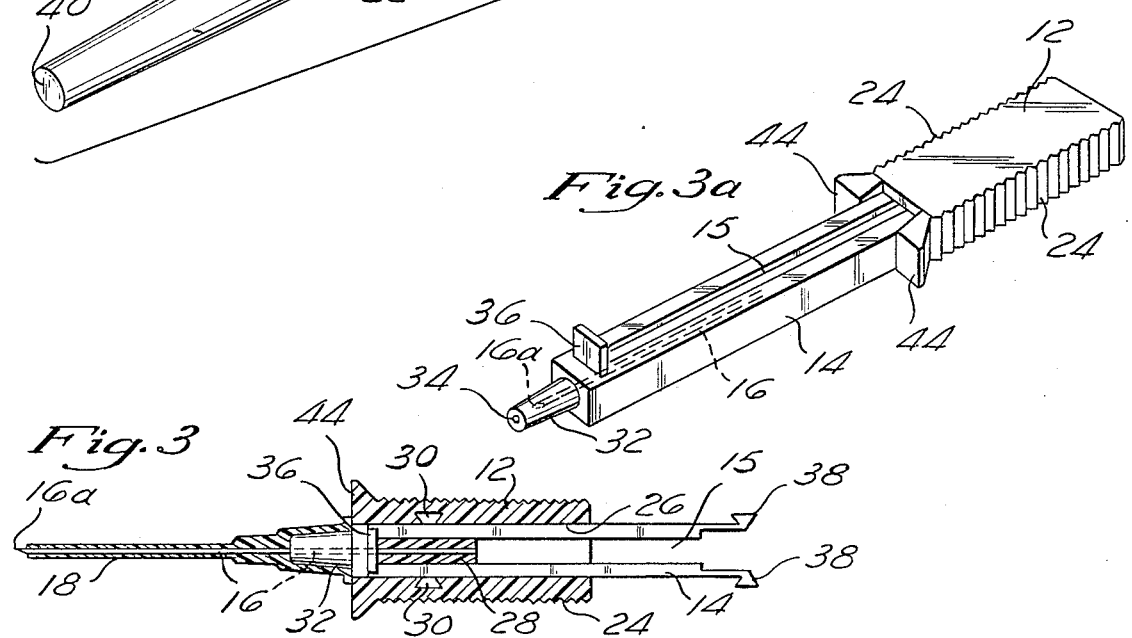

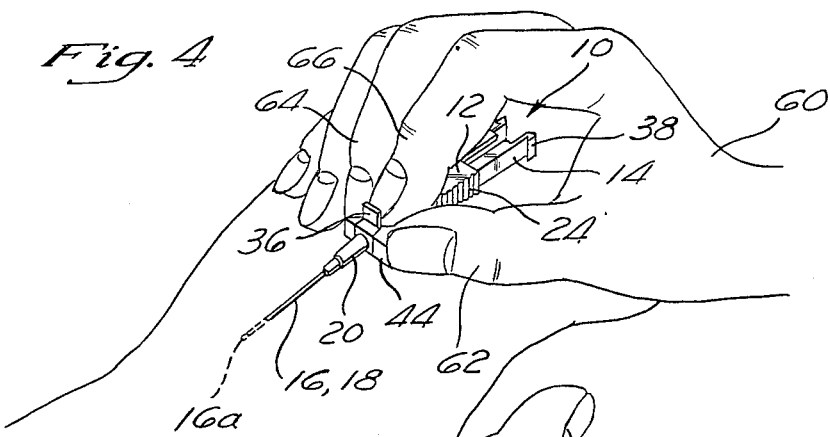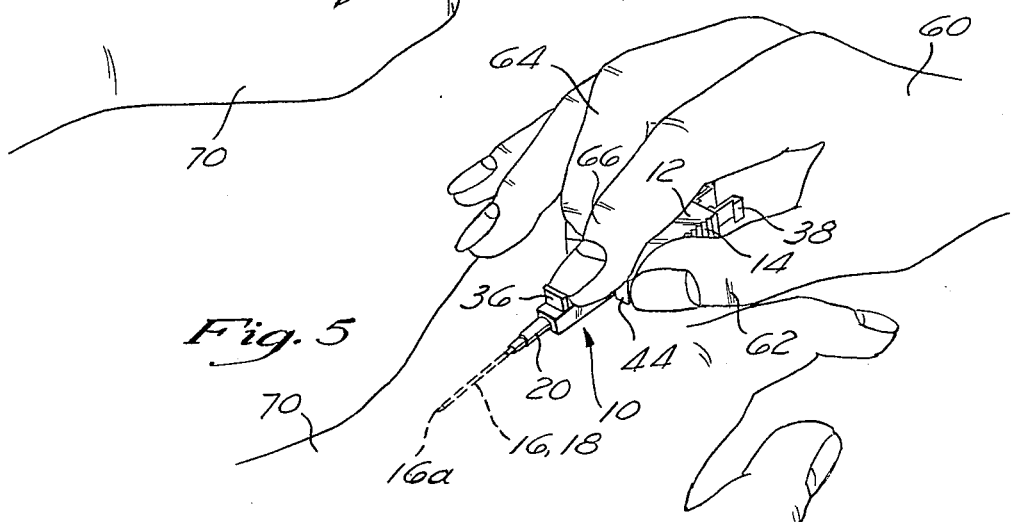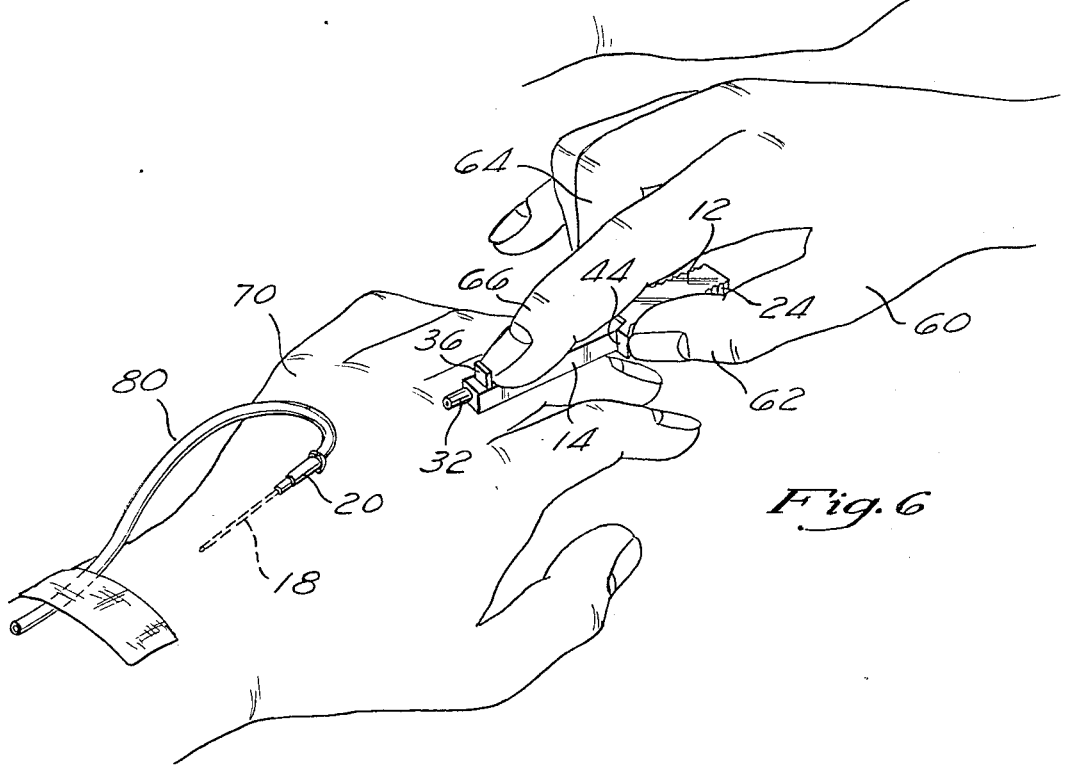

SINGLE HAND ACTUATED LOCKING SAFETY CATHETER AND METHOD OF USE

The subject application is a continuation-in-part U.S. patent application Ser. No. 115,407 filed on Nov. 2, 1987 in the name of Ronald B. Luther, et al., entitled Assembly of Needle and Protector, now U.S. Pat. No. 4,832,696 is a continuation-in-part U.S. patent application Ser. No. 022,132 filed on Mar. 5, 1987 in the name of Luther et al., entitled Assembly of Needle and Protector, now U.S. Pat. No. 4,762,516 the disclosures of which are expressly incorporated herein by reference.

FIELD OF THE INVENTION

The present invention relates generally to medical needles and catheters and more particularly to a single hand actuated locking safety catheter and method use.

BACKGROUND OF THE INVENTION

As is well known in the medical profession, following use of a medical needle, the spent needle is usually manually broken to prevent any inadvertent reuses and disgarded to a biological waste container. However, there is always a small possibility that the spent needle may inadvertently stick or scratch medical health personnel, thereby exposing the medical personnel to substantial health risk. Although such health risks have always been present, the magnitude of such health risks has recently become crictical due to the prevalence of severe infectious diseases such as the HTLV virus (The Acquired Immune Deficiency Syndrome, i.e. AIDS Virus) and Hepatitis.

In recognizing the substantialy safety hazards associated with inadvertent needle sticks, and/or contact with spent medical needles, various devices have recently been introduced into the marketplace, which are designed to cover a spent needle after use. One such device presently being marketed comprises the HR Needle sold by ICU Medical, Inc, of Laguna Hills, California, which functions to almost completely enclose the needle subsequent to use. However, this HR device does not provide a housing or protective cover for the needle tip. This, of course, leaves open the possibility of medical health personnel being accidently stuck or scratched. In addition, the HR Needle, as well as other prior art safety needles, requires medical health personnel to utilize both hands in extending the needle safety cover over the spent needle. During such dual hand manipulation, there is always a possibility that one of the user's hands will slip from the guard device or syringe, whereby an inadvertent needle stick could occur.

As such, there exists a substanatial need in the art for an improved device for preventing an inadvertent needle stick from a spent medical needle, and further which allows the device to be used in a single hand of the user and be manipulated in a simple motion to cover the spent needle.

SUMMARY OF THE PRESENT INVENTION

The present invention specifically addresses and alleviates the above referenced need associated in the prior art and comprises a single hand actuated locking safety catheter and needle assembly and method of use.

More particularly, an assembly of a needle, catheter, and a device for selectively protecting the needle tip from inadvertent needle sticks is disclosed, characterized by use of an elongated housing having a needle extending therefrom, and a needle guard adapted for sliding movement relative the housinng. The needle guard is formed to carry a catheter hub and catheter thereupon and includes an actuation tab to enable selective sliding movement of the needle guard relative the housing and along the length of the needle. The housing is adapted to be held within one hand of the user to permit insertion of the needle and catheter into a patient in a conventional manner. However, after insertion of the needle into the patient, the needle may be withdrawn from the patient and covered by the needle guard merely by pressing agaist the actuation tab with the index finger of the user while slidably retracting the housing and needle relative to the needle guard by use of the thumb and middle finger of user. Upon full retraction of the housing relative to the needle guard, a detent mechanism formed on the housing and guard is engaged to permanently lock the needle guard about the length of the needle and thereby prevent accidental contact with the tip of the needle. Subsequent to use, the spent needle, housing, and needle guard may be disposed of in a biological waste container.

DESCRITPION OF THE DRAWINGS

These, as well as other features of the present invention will be more apparent upon reference to the drawings wherein:

FIG. 1 is a perspective view of the assembled single hand actuated locking safety catheter of the present invention;

FIG. 2 is an exploded perspective view of FIG. 1f

FIG. 3 is a cross-sectional view taken about lines 3-3 of FIG. 2f

FIG. 3A is a perspective view of the single hand actuated locking safety catheter of the present invention depicting the same in its final locked orientation;

FIG. 4 is a perspective view of the present invention being held in the hand of a user with the needle and catheter being inserted into a patient;

FIG. 5 is a perspective view of the present invention illustrating the manner in which the device is manipulated in the single hand of a user to withdraw the needle from the patient; and FIG. 6 is a perspective view of the present invention being manipulated by a single hand of a user to its final locked orientation.

DETAILED DESCRIPTION OF THE PREFERRED EMBODIMENT

Referring to FIG. 1 through 3a, there is shown the single hand actuated locking safety catheter and needle assembly 10 of the present invention composed generally of a handle or housing 12, needle guard 14, medical needle 16 having a sharpened or beveled distal end and an opposing proximal end, catheter 18, catheter hub 20, and needle cover 22, all of which (except for the needle 16) are preferably formed of a plastic material such as medical grade injection molded polycarbonate, or polystyrene. The housing 12 is preferably formed having an elongated rectangular cross-sectional configuration the outside surfaces of which are preferably provided with plural ridges 24 adapted to be grasped by the hand of a user. As best shown in FIG. 3, the interior of the housing 12 is provided with a central channel 26 extending throughout its length and includes a needle mount portion 28 which depends downwardly from the upper surface of the housing 12 adjacent one end thereof so as to be disposed within the interior of the central channel 26. The medical needle 16 is rigidly retained within an axial aperture formed within the needle mount portion 28, and extends outwardly from the housing 12 terminating at a bevelled tip 16(a). The interior sidewalls of the channel 26 formed within the housinng 12 are provided with a pair of slots 30 which form a first portion of the detent mechanism to be described in more detail infra.

The needle guard 14 is preferrably formed as an elongated tubular member having an axial slot or aperture 15 extending substantially throughout the length of it's upper surface which is registered with the needle mount 28 formed within the interior of the housing 12. The needle guard 14 is preferrably fabricated having an external cross-sectional configuration formed in a complimentary configuration to the channel 26 of the housing 12, such that the needle guard 14 may be slidably moved relative the housing 12 along the length of the needle 16. The distal end of the needle guard 14 is provided with a catheter hub mount 32 having a central aperture 34 extending therethrough, the diameter of which is sized to be slightly greater than the diameter of the medical needle 16. An actuation tab 36 extends outwardly from one surface of the needle guard 14 to an elevation beyond the upper surface of the housing 12. The opposite end of the needle guard 14 is provided with a pair of locking ears 38 which are formed in a complimentary configuration to the locking slots 30 formed on the interior walls of the housing 12. The locking ears 38 form the second portion of the locking detent mechanism and are preferrably formed in the manufacturinng process to be biased outwardly in the direction of the arrows indicated in FIG. 3. As will be recognized, this outward biasing is primarily effectuated by using plastic construction materials such as polystyrene and polycarbonate which have flexible memory properties in a thin wall form.

By such construction, it will be recognized that upon relative sliding movement of the needle guard 14, and the housing 12, the needle guard will travel from its relative orientative within the housing 12 as depicted in FIG. 2, to a final orientation depicted in FIG. 3(A). During such sliding movement, the locking ears 38 cam against the interior walls of the channel 26 formed in the housing 12 and upon alignment of the locking ears 38 with the locking slots 30, the locking ears 38 automatically extend in a snapping action into engagement with the slots 30. By such engagement of the locking ears 38 within the locking slots 30, a locking detent mechanism is provided which permanently locks the needle guard 14 to the housing 12 wherein the medical needle 16 is disposed within the interior of the needle guard 14.

The catheter hub 20 and catheter 18 preferrably comprise a conventional luer-lock hub design which is carried upon the length of the needle 16. When positioned upon the length of the needle 16, the catheter hub 20 is registered by engagement with the catheter hub mount 32 formed on the needle guard 14. In addition, with the catheter hub 20 and catheter 18 carried upon the device 10, only the tip 16(a) of the medical needle 16 extends beyond the end of the catheter 18 to allow insertion of the needle 16 and catheter 18 into a patient.

The cover 22 is preferrably formed having an elongate frusto-conical shape configuration terminating at a closed end 40. The opposite end of the cover 22 is provided with a pair of wings 42 which are sized to extend over a pair of locking ears 44 formed adjacent one end of the housing 12. As will be recognized, the cover 22 is formed to have an axial length and interior diameter sufficient to cover the catheter hub 20, catheter 18 and medical needle 16 when the same are assembled together.

With the structure defined, the method of utilizing the single hand actuated locking safety catheter and needle assembly 10 of the present invention, may be described with specific reference to FIGS. 4, 5, and 6. Preparatory to use, the cover 22 is removed from the housing 12, thereby exposing the needle tip 16(a) catheter 18, and catheter hub 20, which is carried on the catheter hub mount 32 of the needle guard 14. A user, typically a medical technician, may then grasp the handle or housing 12 with one hand 60 and insert the protruding distal needle tip 16(a) and catheter 18 into the patient 70 in a conventional manner, as depicted in FIG. 4. Typically, the ridged side edges 24 of the housing 12 are grasped between the thumb 62 and middle finger 64 of the user's hand 60 with the index finger 66, being positioned behind the actuation tab 36. Due to the engagement of the rear surface of the actuation tab 36 with the upper surface of the housing 12, rearward or proximally directed sliding movement of the needle guard 14 relative the housing 12 is prohibited, thereby allowing the needle 16 and catheter 18 to be easily inserted into the patient 70 as depicted in FIG. 4. Additionally, when the needle 16 and catheter 18 is properly inserted into the patient, the viewing of blood flashback within the aperture formed within the needle mount 28 is facilitated due to the housing 12 and needle guard 14 preferrably being formed from a transparent or semitransparent material.

With the catheter 18 and catheter hub 20 remaining in the patient 70, the needle 16 may be withdrawn proximally from the interior of the catheter 18 by the user merely pressing or applying moderate distally directed pressure upon the rear surface of the actuation tab 36 with the index finger 66 while slidably retracting or proximally withdrawing the housing 12 along the length of the needle guard 14 by way of the thumb and middle finger 62 and 64 as illustrated in FIG. 5. As will be recognized, in view of the handle or needle 16 being mounted to the housing 12, during the sliding motion of the housing 12 relative the needle guard 14, the needle is withdrawn from its first needle position within the interior of the catheter 20 and disposed in a second needle position within the interior of the needle guard 14.

Continued sliding movement of the housing 12 relative the needle guard 14 causes the locking ears 38 to engage the complimentary shaped locking slots 30 formed within the interior of the housing 12 whereby the locking ears 38 automatically snap into the slots 30 forming a locking detent wherein the complete length of the needle 16 is diposed in a second needle position within the interior of the needle guard 14 (as best depicted in FIG. 3(A). The entire assembly 10 may then be safely removed from the patient as illustrated in FIG. 6 and subsequently be disgarded in a biological waste container. As will be recognized, the disgarding of the assembly 10 may be effectuated without fear of any inadvertent needle stick in veiw of the fact that the guard 14 extends completely about and encloses the needle 16, with the position of the needle guard 14 relative the housing being maintained by the lock detent mechanism. Subsequently, a conventional fluid line 80 may be attached to the hub 20 of the catheter remaining with the patient 70.

From the above, it will be recognized that the present invention comprises a significant improvement in the art by allowing insertion of the catheter into the patient and subsequent withdrawal of the needle from the patient while allowing the catheter to remain therein by use of a single hand and a simple hand manipulation. Additionally, it will be recognized that the withdrawal of the needle 16 from the patient may be effectuated without ever exposing the needle to the medical user, since the catheter hub mount 32 of the needle guard 14 may be maintained in engagement with the catheter hub 20 and not disengaged therefrom until such time as the entire needle 16 is disposed with the interior of the needle guard 14. Further it will be recognized that due construction and method of utilizing the present invention, a user may withdraw and subsequently lock the needle within the interior of the needle guard by use of a single hand and in a simple manipulative fashion.

Although for purposes of description, certain materials configurations and methodologies have been disclosed herein, those skilled in the art will recognized the various modifications to the same can be made without departing from the spirit of the present invention and such modification clearly contemplated herein.

What is claimed is:

1. An over-the-needle catheter assembly comprising:
   a housing including sidewalls and a first portion of a detente lock;
   a needle mounted to said housing and extending therefrom;
   a needle guard slidably mounted to said housing including a second portion of a detente lock;
   a catheter hub support formed on said needle guard;
   a catheter mountable upon said needle, said catheter having a catheter hub sized to be registered upon said catheter hub support such that, following insertion of said needle and said catheter into a patient:
   (i) said housing and said needle may be concomitantly retracted relative to said needle guard, said concomitant retraction of said housing and said needle being operative to withdraw said needle from said catheter and into said needle guard, and, thereafter;
   (ii) said catheter hub may be separated from said catheter hub support allowing the housing, needle guard, and the needle positioned with said needle guard to be separated from the patient while the catheter and cateter hub remain with the patient.

2. The assembly claim 1 further comprising an actuation tab formed on said needle guard extending outwardly beyond said housing.

3. The assembly of claim 2 wherein said housing is sized and configured such that it maybe grasped with one hand of a user.

4. The assembly of claim 3 wherein said actuation tab is sized, configured, and positioned such that it may be pressed in a first direction toward said catheter with one finger of said one hand of said user while said housing is slidably moved in a second direction, opposite said first direction, by said one hand of said user.

5. The assembly of claim 4 wherein said needle guard is formed having a length sufficient to extend completely over the length of said needle prior to separation of housing and needle from said catheter and catheter hub.

6. The assembly of claim 5 wherein said housing is sized and configured to be grasped between the thumb and middle finger of said one hand of said user.

7. The assembly of claim 6 wherein said housing and said actuation tab are sized, configured, and positioned such that the index finger of said hand may be pressed against said activation tab in said first direction while the thumb and at least one other finger of said hand are employed to grasp said housing and to slidably move said housing in said second direction.

8. A method of administering a catheter to a patient comprising the steps of:
   grasping a housing having a needle and catheter extending therefrom and a needle guard slidably mounted to said housing;
   inserting said needle and said catheter into a patient by urging said housing toward said patient;
   retracting said housing to withdraw said needle from said catheter while maintaining said catheter within said patient, said retraction being accomplished by holding said housing in one hand and manually sliding said housing with said one hand, relative said needle guard, to a locked positioned wherein said needle is enclosed withn said needle guard, and, thereafter;
   removing said locked needle, needle guard and housing from said catheter.

9. The method of claim 8, wherein said retracting step comprises:
   pressing said needle guard in a first direction toward said catheter with one finger of said one hand of said user; and
   sliding said housing in a second direction opposite said first direction with said one hand of said user.

10. The method of claim 9 wherein said sliding of said housing in said second direction is continued until a locking detent mechanism formed between said housing and said needle guard is engaged.

11. The method of claim 10 wherein said needle guard includes an actuation tab and said pressing step comprises pressing said actuation tab in said first direction toward said catheter.

12. The method of claim 11 wherein said pressing step comprises pressing said actuation tab with the index finger of said user in said first direction toward said catheter.

13. The method of claim 12 wherein said sliding step comprises sliding said housing in said second direction, opposite said first direction by movement of the thumb and middle finger of said one hand of said user.

14. A method of administering a catheter to a patient comprising the steps of:
   grasping a housing having a needle extending therefrom and a needle guard slidably mounted to said housing which engages a catheter disposed upon the length of said needle;
   inserting said needle and said catheter into a patient by urging said housing in a first direction toward said patient;
   retracting said needle from said catheter while maintaining said catheter in engagement with said needle guard by holding said housing with one hand and manually sliding, with said one hand, said housing relative said needle guard in a second direction opposite said first direction to enclose said needle within said needle guard, and, thereafter;
   disengaging said needle guard with said needle enclosed therein from said catheter to permit subsequent removal of the housing, needle guard and needle while said catheter remains within said patient.

15. The method of claim 14 wherein between said retracting and disengaging steps said method comprises the further step of locking said housing to said needle guard by sliding said housing in said second direction to a position wherein a detent mechanism formed between said housing and said needle guard is engaged.

16. The method of claim 15 comprising the further step of removing said locked needle, needle guard and housing from said catheter.

17. A percutaneously insertable over-the-needle catheter assembly, said assembly comprising:
   a tubular catheter having a proximal end, a distal end, and a tubular lumen extending axially therethrough;
   a needle having a proximal end and a sharpened distal end, said needle being positionable in a first needle position wherein the needle is axially disposed within the lumen of the tubular catheter and the sharpened distal end of the needle extends beyond the distal end of the tubular catheter;
   a needle guard having an interior needle receiving passage formed therein, said needle guard being positioned relative to said needle such that said needle is axially retractable from said first needle position to a second needle position wherein at least a portion of said needle is diposed within said needle receiving passage and further wherein the sharpened distal tip of said needle is shielded by said needle guard;
   a handle attached to said needle, said handle being sized and configured to be graspable by a human hand facilitate manual pulling of said needle from said first needle position to said second needle position; and
   said handle and said needle guard being cooperatively sized and configured to frictionally engage one another when said needle has reached said second needle position, said frictional engagement of the handle and needle guard being operative to hold said handle is a fixed position relative to said needle guard, thereby holding said needle in said second needle position.

18. The catheter assembly of claim 17 further comprising a finger engagement tab attached to and extendig outwardly from said needle guard.

19. The catheter assembly of claim 17 wherein said handle is sized and configured to be grasped between the thumb and third finger of the human hand.

20. The catheter assembly of claim 18 wherein:
   said handle is sized and configured to be grasped between the thumb and third finger of one human hand; and
   said finger engagement tab is sized, configured and positioned such that the second finger of said one hand may be positioned against said tab while said handle is grasped between the thumb and third finger of said one hand.

21. The catheter assembly of claim 17 wherein the said handle and said needle guard further comprise:
   a first detente lock portion formed on the needle guard; and
   a second detente lock portion formed on the handle;
   said first and second detente lock portions being positioned and configured to engage one another when said needle reaches said second needle position, thereby locking said needle in said second needle position.

* * * * *